United States Patent [19]

Rizzo

[11] Patent Number: 5,141,748
[45] Date of Patent: Aug. 25, 1992

[54] IMPLANT DRUG DELIVERY DEVICE

[75] Inventor: Vincent J. Rizzo, No. Arlington, N.J.

[73] Assignee: Hoffmann-La Roche, Inc., Nutley, N.J.

[21] Appl. No.: 312,084

[22] Filed: Feb. 17, 1989

[51] Int. Cl.$^5$ ............................................. A61F 2/00
[52] U.S. Cl. .................... 424/425; 424/422; 424/423; 424/424; 424/426
[58] Field of Search ............... 424/425, 424, 422, 423, 424/426

[56] References Cited

U.S. PATENT DOCUMENTS

| | | | |
|---|---|---|---|
| 3,279,996 | 10/1966 | Long, Jr. et al. | 424/424 |
| 4,191,741 | 3/1980 | Hudson et al. | 424/425 |
| 4,331,651 | 4/1982 | Reul | 424/19 |
| 4,351,337 | 9/1982 | Sidman | 424/424 X |
| 4,666,704 | 5/1987 | Shalati | 424/19 |
| 4,814,184 | 3/1989 | Aguadisch | 424/486 |

FOREIGN PATENT DOCUMENTS

| | | | |
|---|---|---|---|
| 0013949 | 8/1980 | European Pat. Off. | 424/425 |
| 2207355 | 2/1989 | United Kingdom . | |

Primary Examiner—Thurman K. Page
Assistant Examiner—D. Gabrielle Phelan
Attorney, Agent, or Firm—George M. Gould; William H. Epstein

[57] ABSTRACT

A drug delivery device for subcutaneous implantation in animals having the ability to deliver drug at a controlled rate over a prolonged period of time, comprising a rod shaped polymeric inner matrix with an elongated body and two ends, said matrix having solid particles of the drug to be delivered dispersed throughout the matrix and a polymeric outer membrane wherein the membrane is chemically bound to the surface of the elongated body of the matrix and methods for forming said device.

7 Claims, 3 Drawing Sheets

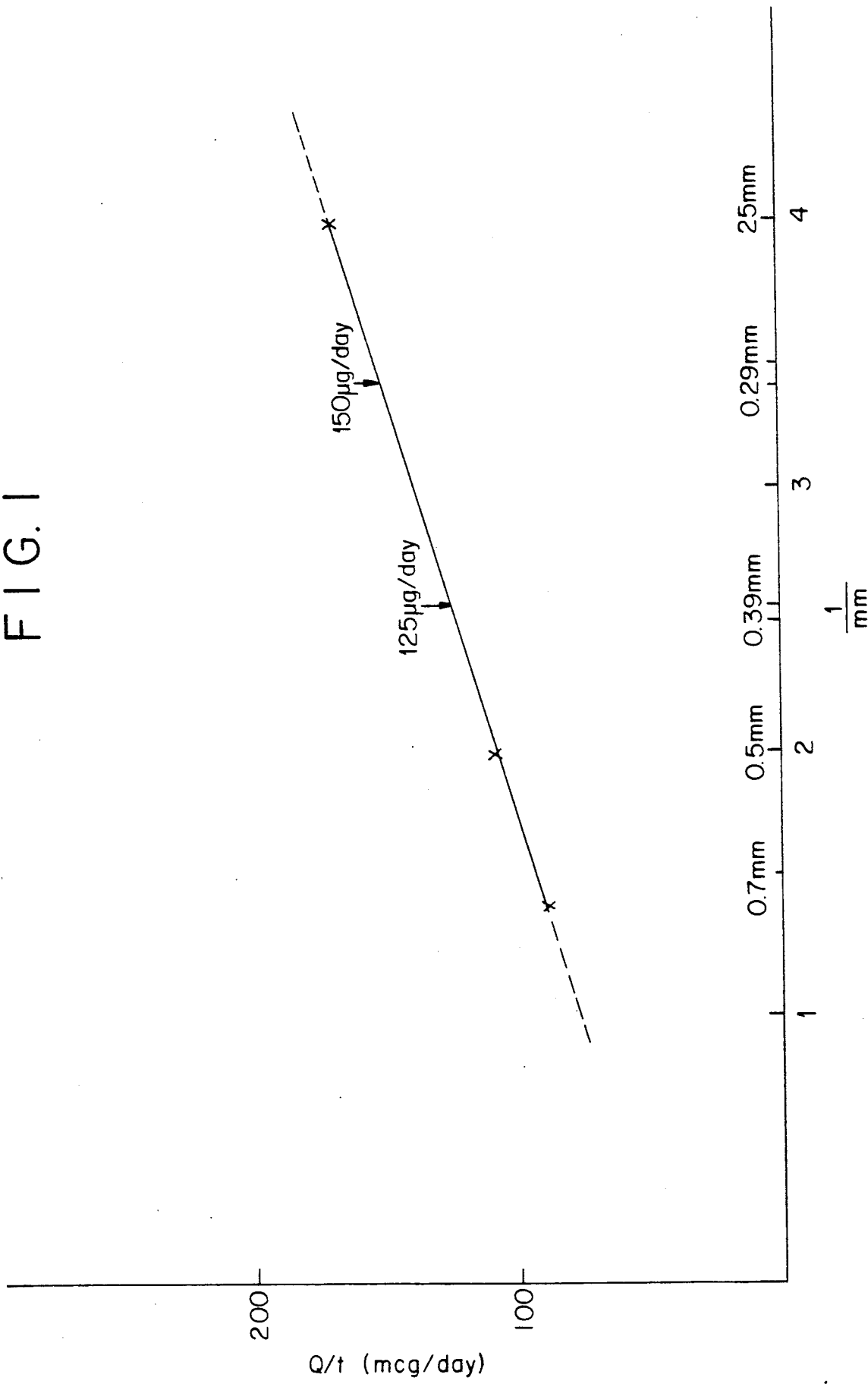

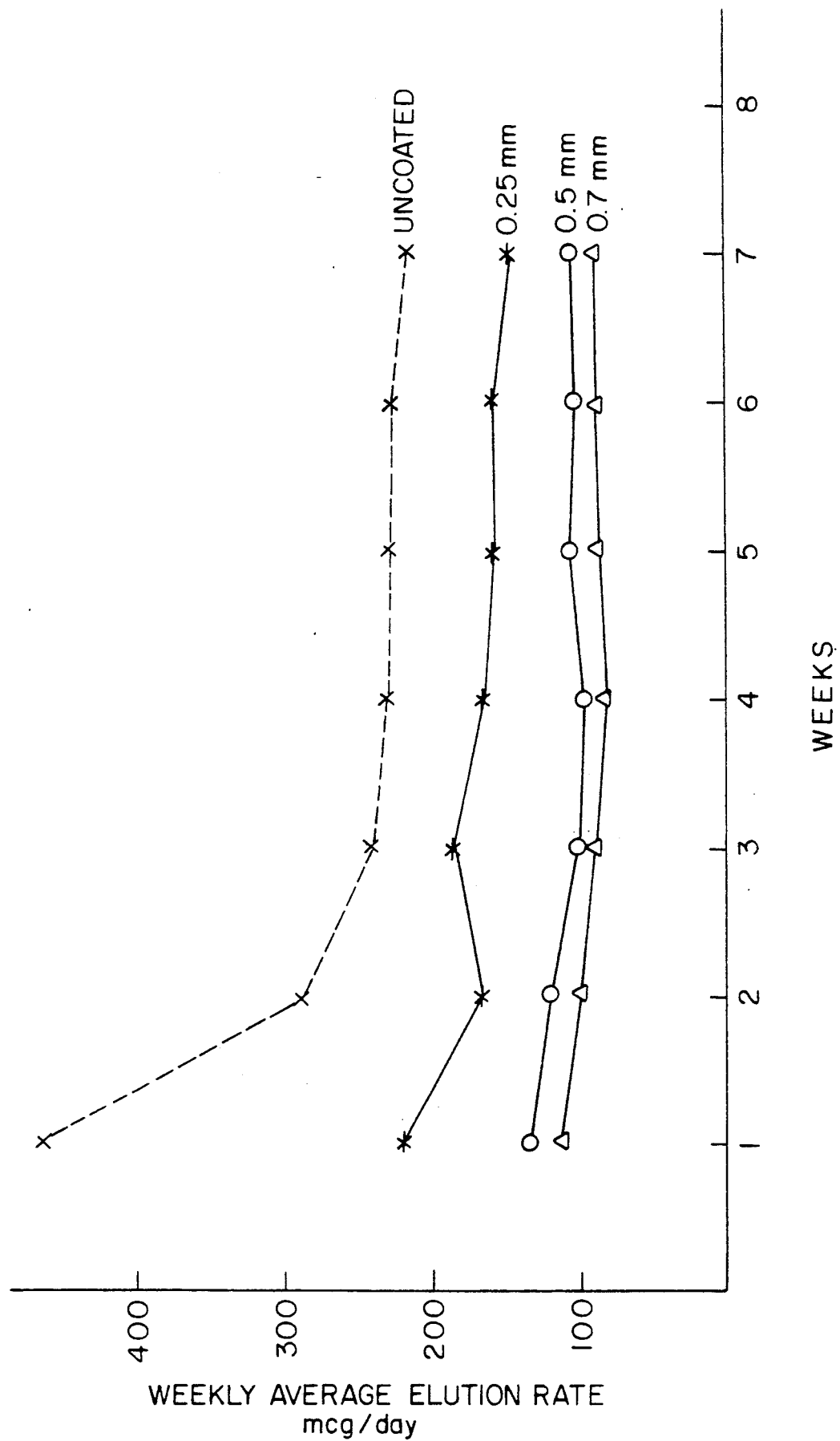

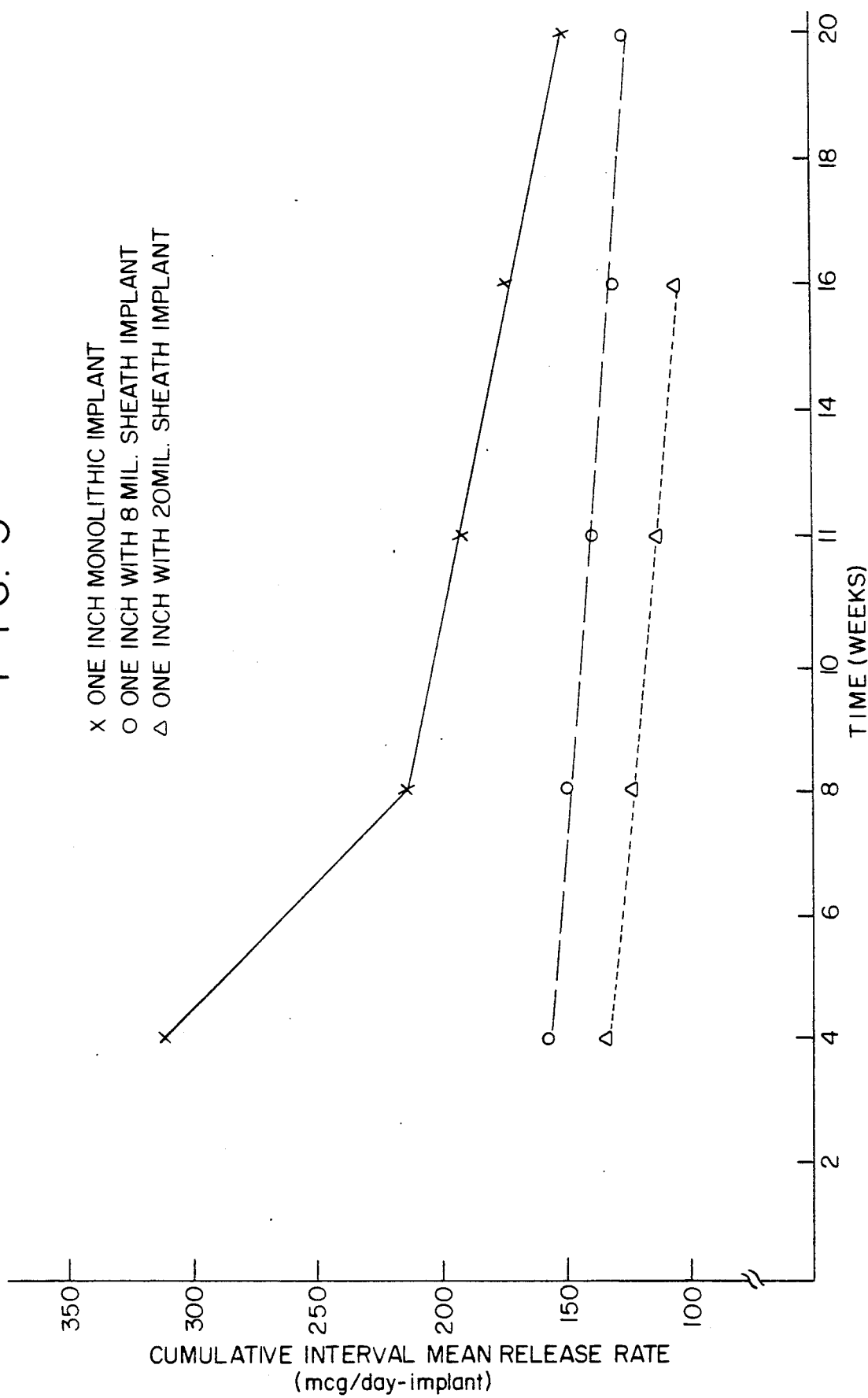

IMPLANT DRUG DELIVERY DEVICE

BACKGROUND OF THE INVENTION

The use of implant devices is becoming important with regard to the administration of drugs or pharmaceuticals particularly to animals raised for the human food supply. In general, these devices containing the pharmaceutical or drugs to be administered are subcutaneously implanted in the animal and the pharmaceuticals or drugs are administered to the animal over a prolonged period of time in a predetermined and controlled quantity. By use of implant devices, it is not necessary to repeatedly administer the pharmaceutical material daily to the animal in question. In this way whole herds of cattle or other animals raised for human food purposes can be simultaneously implanted with a device containing a pharmaceutical so that device releases the pharmaceutical to the animal over a prolonged period of time.

It has been difficult to construct implants with a zero order timed dependence rate of release. A zero order timed dependence rate of release occurs when a constant controlled amount of the pharmaceutical is released daily to the animal. In most cases, implants provide an initial burst of drug release which slowly tapers off with time. Such variable rates of release are extremely disadvantageous, since they do not provide the proper controlled dosing to be administered to the animal. Therefore, it has been long desired to provide a drug delivery device for subcutaneous implantation, which can release the drug with minimum initial burst and at a controlled rate which does not substantially vary with time.

Various devices have been proposed for solving this problem. However, none have been entirely satisfactory. As set forth in U.S. Pat. No. 3,710,795, Higuchi et al., Jan. 16, 1973, these devices generally constitute an inner matrix carrying the pharmaceutical material or drug to be administered, and a polymeric membrane permeable to the passage of this therapeutic material or drug by diffusion. In the device of Higuchi, et al., the matrix is sealed within a heat shrinkable stretched polymeric membrane formed about the matrix. As this matrix contracts, some of the drug is removed therefrom, forming gas pockets or voids which can slow-up the release of the drug through the membrane and introduce an uncontrollable factor into the drug release mechanism.

In order to solve this problem, Chien, et al. in U.S. Pat. Nos. 3,946,106, Mar. 23, 1976; 3,992,518, Nov. 6, 1976; and 4,053,580, Oct. 11, 1977 disclose utilizing a pharmaceutical delivery device with a heat shrinkable membrane where the matrix contains microsealed compartments containing the pharmaceutical in a hydrophilic solvent system. This system, as disclosed in U.S. Pat. No. 4,472,394, Sep. 18, 1984—Peterson, is used for administering steriods, in particular 17-acetoxy-11$\beta$-methyl-norpregn-4-ene-20-dione (norgestomet) for controlling estrus in female cattle. It has been found that while the matrix of this delivery system does not shrink in volume due to the presence of microsealed compartments, the diffusion rate of the pharmaceutical from these compartments is insufficient to allow a controlled rate of release of the drug or pharmaceutical for an extended period of time.

SUMMARY OF THE INVENTION

This invention is directed to a controlled release drug delivery device capable of administering a drug over a prolonged period of time and adapted for subcutaneous implantation. The implant device of this invention contains an inner matrix having solid particles of a drug dispersed throughout the matrix and an outer membrane chemically bonded to the outer surface of the matrix. Both the matrix and membrane are formed from polymeric materials which can be cured or cross-linked through the use of same cross-linking agent and catalyst. Both the inner matrrix and the outer-polymeric membrane are permeable to passage of the drug by diffusion and the drug diffuses through outer polymeric membrane at a lesser rate so that passage through the outer polymeric membrane is the drug releasing rate controlling step. It has been found that by chemically bonding the membrane throughout its surface to the matrix, the matrix is held in place by the polymeric membrane so that the drug is released without the formation of air pockets or shrinkage. In this manner the device of this invention provides a uniform rate of release of the drug over a prolonged period of time. By the unique, direct chemical bonding of the inner matrix to the outer membrane, an improved implant is produced which has superior properties as to constant controlled rate of release of the drug over a prolonged period of time.

BRIEF DESCRIPTION OF THE DRAWINGS

In the Drawings:

FIG. 1, is a graph of the results of an in vitro study comparing the average daily release rate of norgestomet implants containing film sizes of various thickness;

FIG. 2, is a graph of the results of an in vitro study comparing the rate of release, over an eight week period, of implants of this invention with implants having no film.

FIG. 3, is a graph of the results of an in vivo study comparing the rate of release in cattle of norgestomet implants of this invention having film thicknesses of various sizes with a non-film norgestomet implant.

DETAILED DESCRIPTION OF THE INVENTION

This invention is directed to a rod shaped implant device for delivering a drug over a prolonged or extended time period, which device is adapted to be implanted subcutaneously.

The implant device of this invention contains a rod shaped inner matrix, said matrix having an elongated body and two ends with solid particles of a drug dispersed throughout and an outer membrane chemically bonded to at least the surface of the elongated body of the matrix. Both the matrix and membrane which form the device of this invention are formed from organic polymers which can be cured or cross-linked through the use of the same cross-linking agent and catalyst for cross-linking.

In accordance with this invention, both the inner matrix and the outer membrane of the implant are formed from polymers which can be cross-linked with the same cross-linking agent and catalyst. This produces chemical bonding between matrix and the membrane when curing of either or both the membrane and matrix is carried out while the membrane and matrix are in contact. In accordance with this invention, the implant device of this invention is produced when curing of either or both the membrane and the matrix is carried out while the membrane contacts the outer surface of the elongated body of the matrix. In this manner, curing either the membrane or matrix with a cross-linking agent and catalyst not only cross-links the matrix or the membrane but also cross-links the matrix to the membrane to form a chemical bond between the matrix and the membrane. In the preferred implant of this invention, the implant consists of an elongated body and upper and lower ends with the membrane enclosing the outer surface and the ends of the implant having no outer membrane. However, if desired the ends of matrix may be sealed by placement of the membrane around the ends.

In accordance with this invention, any conventional polymeric materials which can be cross-linked by the same cross-linking agent and catalyst can be used for the matrix and the membrane. Among the preferred materials are the siloxane polymers with copolymers of methyl vinyl siloxane and dimethylpolysiloxane being especially preferred.

In accordance with a particularly preferred embodiment of this invention, the copolymers of methyl vinyl siloxane and dimethylpolysiloxane which form the implant device of this invention are cured (cross-linked) by a hydrosylation reaction. Through the use of an organohydrogen siloxane cross-linking agent, preferably an alkyl hydrogen siloxane cross-linking agent, hydrosylation occurs across the vinyl double bond in the presence of a platinum catalyst during the curing step. This cross-linking, while occurring in the copolymers of methyl vinyl siloxane and dimethylpolysiloxane which form both the matrix and/or the outer membrane, occurs also between the copolymer of the matrix and the copolymer of the membrane. This forms a permanent chemical bond directly connecting the surface of the inner matrix to the outer membrane. In this manner, the outer membrane is adhered to the matrix by chemical bonding throughout at least the entire surface of the elongated body of the implant device. In forming the preferred matrix and the membrane of this invention, any copolymer of methyl vinyl siloxane and dimethylpolysiloxane, which has residual vinyl groups which may be cross-linked by organohydrogensiloxane cross-linking agent, preferably an alkyl hydrogensiloxane, catalyzed by a platinum catalyst, can be utilized. These copolymers and their curing systems are well known and disclosed in U.S. Pat. No. 3,445,420—May 20, 1969, and U.S. Pat. No. 4,162,243—Jul. 24, 1979. These copolymers are referred to as biologically acceptable or medical grade polydimethylvinylsiloxanes.

Among the preferred copolymers of methyl vinyl siloxane and dimethylpolysiloxane which form the matrix are those sold by Dow-Corning as MDX 4-4210; Q7-4840; Q7-2218; Q7-4735; Q7-4750 and Q7-4765. Polymers such as Q7-4840 are a two part resin system with one part being a paste containing the copolymer in an inert carrier and the other part containing the cross-linking agent and the catalyst for this polymer. The cross-linking agent for this copolymer is an organohydrogensiloxane and the catalyst is a platinum catalyst. Any conventional organohydrogensiloxane cross-linking agent can be utilized in the formation of the polydimethylvinylsiloxane polymer matrix of this invention. Among the organohydrogensiloxane cross-linking agents are those set forth in column 6, lines 29 to 58 of U.S. Pat. No. 4,162,243. The preferred organohydrogensiloxanes are the alkylhydrogensiloxane with methyl being the preferred alkyl group. The alkyl group generally contains from 1 to 6 carbon atoms.

Any of the platinum catalysts for activating these cross-linking agents to cross-link siloxane polymers can be utilized in accordance with this invention. Organohydrogensiloxane cross-linking agents and platinum catalyst for these cross-linking agents are well known in the art. See U.S. Pat. No. 4,162,243.

In forming the outer membrane in which the elongated body of the inner matrix is disposed, in accordance with the most preferred implant device of this invention, any conventional siloxane polymer in the form of a film can be utilized as the membrane or film, provided the siloxane can be cross-linked with an organohydrogensiloxane cross-linking agent catalyzed by a platinum catalyst. Forming the inner matrix and the outer polymeric membrane from a polymer which can be cured in the same manner allows one upon curing to form a permanent chemical bond between the copolymer in the matrix and the copolymer in the outer membrane.

In preparing the matrix in accordance with a preferred embodiment, the polymeric material, generally in the form of a paste, is admixed with the curing agent. The curing agent is preferably a mixture of the cross-linking agent and the platinum catalyst. In forming the matrix, a mixture is formed by disbursing solid particles of the drug into the mixture of the cross-linking agent and the polymeric material to be cross-linked upon curing.

In forming the outer polymeric membrane, either a film or coating of the polymeric material can be utilized. If it is desired to produce the outer polymeric membrane as a film, the mixture of the polymer to be cross-linked and the cross-linking agent having the drug dispersed therein is placed inside a film formed from a polymer which is cured by the same cross-linking agent as the polymer in the matrix. After placing the matrix mixture into the polymeric film, the film containing the matrix mixture, in accordance with a preferred embodiment, is placed into polymeric tubing from which it is removed after curing of the matrix mixture and the film has taken place. The polymeric tubing acts as mold for the polymeric matrix and the polymeric film during the curing step to facilitate the chemical bonding of the matrix to the polymeric film through cross-linking during the curing step. In addition, the mold establishes the size and the rod like shape of the implant achieved during the curing step. After curing, the polymeric tube is removed, leaving an implant where the outer film is directly adhered through chemical bonding to the cross-linked inner matrix having the drug dispersed throughout.

Any conventional material can be utilized as the tubing for providing the mold in accordance with the preferred embodiment of this invention. Among the preferred materials for use in this invention are polyethylene, polypropylene, neoprene rubbers, chlorinated polyethylene, butylrubber, epichlorohydrin rubbers and the like. Any conventional method of curing can be utilized in curing the matrix so as to form the solid rod shaped polymeric matrix, having the drug dispersed therethrough, adhered through chemical bonding to the outer film.

When Silastic ® polymeric materials are utilized, any conventional method for curing these Silastic ® polymeric materials with cross-linking agents can be utilized in accordance with this invention. Generally, the polymeric material and the cross-linking agent can be cured by allowing this mixture to sit at room temperature for at least about 7 days. On the other hand, curing can be accomplished in a much shorter time by utilizing elevated temperatures, i.e. temperatures of at least 30° C. If temperatures above about 100° C., such as from about 100° to 150° are utilized, curing is accomplished in a shorter time. It is generally preferred to use temperatures of from about 30° C. to about 80° C. for a period of from about 6 hours to about 5 days. In carrying out the curing step, shorter periods with higher temperatures can be used. Therefore, the preferred period of curing varies inversely with the temperature utilized.

In accordance with another embodiment of this invention, the outer membrane of polymeric material can be formed as a coating which is uniformly bonded to the rod shaped matrix containing the drug dispersed therein. In accordance with this embodiment, the matrix is formed and cross-linked in a polymeric tube as described above without the presence of the film. Therefore, curing of the matrix takes place without the presence of the membrane. The membrane is placed on the cured solid matrix by the use of conventional coating techniques. A preferred coating technique, in accordance with this embodiment, involves dipping the cross-linked rod shaped matrix into a solution containing the polymeric material which forms the outer coating and the cross-linking system for this polymer. The preferred polymeric materials for forming the membrane are copolymers of methyl vinyl siloxane and dimethylpolysiloxane and the preferred cross-linking system contains an organohydrogensiloxane cross-linking agent and platinum catalyst for activating this cross-linking agent. The rod shaped matrix coated with this solution is then cured to form the membrane utilizing conventional curing conditions such as those described hereinbefore. Curing produces an outer membrane of polymeric material through the use of the cross-linking agent. Such curing not only cross-links the polymeric material which forms the membrane but also causes cross-linking of this polymeric material of the membrane to the polymeric material in the elongated body of the inner matrix. In this manner, the polymeric membrane is chemically combined with and bonded to the surface of the elongated body of the matrix. The thickness of the polymeric membrane can be made to any desired dimension by repeating the coating and curing steps. In this manner, the polymeric membrane can have any desired thickness.

The polymeric membrane should be of such a thickness so that the drug, which is dispersed throughout the matrix, can pass through the membrane by diffusion. Therefore the membrane must be permeable so that the drug can pass through. In accordance with this invention, it has been found that membranes having thicknesses of about 0.1 mm to about 0.7 mm are especially suitable for this purpose. By varying this thickness, one can control the amount of drug released into the system of the animal. The thicker the membrane, the slower the rate of release of the drug into the systems.

A wide variety of pharmaceuticals or drugs may be administered by the implants of this inventions: steroids, alkaloids, fatty acids, vitamins, antibiotics and birth control agents. Among the preferred drugs are the drugs utilized for controlling estrus and promoting growth. The drugs which control estrus are drugs which initiate the onset of puberty in female domestic animals. Among the drugs which can be administered by the implant of this invention are those drugs listed in columns 7 and 8 of U.S. Pat. No. 3,710,795. The preferred drugs for administration in accordance with the implant of the invention is norgestomet, lasalocid, monensin and melengestrol acetate. While the implant device of this invention can be utilized for domestic animals such as cats and dogs, it is preferably used for animals raised for food purposes, particularly, pigs, cows, sheep, chickens, etc. The device is ideally suited for sports animals, such as horses.

The amount of drug incorporated into the drug delivery device of this invention varies depending upon a particular drug, the desired therapeutic affect and the desired time span. Since a variety of devices in a variety of sizes and shapes are intended to provide dosage regimens for therapy for a variety purposes, there is no critical upper limit in the amount of drug incorporated into the device. The lower limit too will depend upon the activity of the drug and the time span of its release from the device. Those skilled in the pharmaceutical arts will know how to determine toxic levels of a given drug as well as the minimum effective dose. With this information a proper dose form can be prepared by measuring the in vivo rate of a given pharmaceutical by standard analytic techniques. In some cases and in particular norgestomet, the matrix contains from 5% by weight to about 25% by weight based upon the weight of the matrix of the drug and from about 95% by weight to about 75% by weight of the polymeric material in which the solid drug is dispersed.

The following examples will serve to illustrate the invention without in anyway being limitative thereof. The viscosity given is measured at room temperature i.e. about 25° C.

EXAMPLE 1

34.8 grams of a paste having a viscosity of 800,000 cps and containing a medical grade copolymer of methyl vinyl siloxane and dimethylpolysiloxane polymer (MW 50,000) and silicon dioxide and 34.8 grams of a silicon dioxide paste having a viscosity of 1,440,000 cps containing a curing agent for the siloxane copolymer which contains a platinum catalyst and methylhydrogensiloxane cross linking agent were placed on two rolls of a triple roller mill, having the gap set at 1.5 mill. Both the copolymer and the curing agent are sold as a two part system by Dow-Corning as Q7-4840. Norgestomet crystals (14.4 grams) were spread into paste mixture and the resulting mixture was passed three times through the mill. After milling the paste containing norgestomet was removed from the mill and placed on a large glass plate measuring 10" by 25". On this plate, the norgestomet containing silastic paste was levigated for three periods of five minutes each using two 10" stainless steel spatulas to obtain a homogeneous paste. This homogeneous paste was deairated first in a vacuum chamber at a pressure of 25 microns of mercury for 30 minutes and then finally by centrifuging at 1,000 RPM for one hour. For the centrifuging, the homogeneous paste was transferred to a metal syringe having an internal diameter of 3.8 cm and a length of 16 cm.

Hollow polyvinyl chloride tubing having an internal diameter of 3.5 mm and a external diameter of 5.0 mm was cut into 16" lengths. The hollow of this tubing was cleaned by blowing air through. Into each of the 16" lengths of polyvinyl chloride tubing, there was placed a hollow film of 0.2 mm thickness. This film was a copolymer of methyl vinyl siloxane and dimethylpolysiloxane purchased from Dow-Corning as RX-50 (Q-4750). This film, as purchased, had been already cured with a methylhydrogensiloxane cross-linking agent, and a platinum catalyst.

The siloxane film contained within the polyvinyl chloride tubes were filled with the deairated norgestomet containing paste using a hydraulic jack to push the paste out of the syringe through a 3.4 mm die fitted with the polyvinylchloride RX-50 tubing. The filled polyvinyl chloride tubes were placed in a hot air oven and allowed to cure at 60° C. for 3 days. After this period the polyvinylchloride tubes were removed from the oven and the polyvinylchloride tubing was removed leaving an implant containing a solid matrix chemically bonded to a siloxane film having a thickness of 0.2 mm. The 0.2 mm film (8 mil sheath) could not be removed from the matrix of the implant. The implant was cut into 400 single implants of 1" in length. Each implant contained 36 mg of norgestomet.

EXAMPLE 2

Implants one inch in length and 3.5 mm were made by the same procedure as Example 1, except that no siloxane film was used. Therefore, the matrix without any film was placed inside the polyvinyl chloride tube. After curing the matrix was removed from the tube. The implant had no film but was merely the matrix comprised of norgestomet dispersed in this polydimethylvinylsiloxane matrix.

EXAMPLE 3

Implants containing 50 mg of norgestomet were made by procedure of Example 1 except that 50 mg of norgestomet was added per 80 mg of each of the two parts of the Q7-4840 Silastic ® system. The implants in this product contained 50 mg of norgestomet per 1" implant.

EXAMPLE 4

Implants containing less than 30 mg of norgestomet per implant were made by adding 20 mg of norgestomet per 95 mg of each part of the two parts of Q7-4840 Silastic ® system by the procedures of Example 1. The implants thus produced by following the procedure of Example 1 contained 20 mg of norgestomet per 1" implant.

EXAMPLE 5

Implants of varying doses were produced by cutting the cured implant produced in Example 1 into sizes greater and smaller than 1". A 0.5" implant contained 18 mg of norgestomet; whereas a 1.5" implant contained 54 mg of norgestomet.

EXAMPLE 6

Implants of varying release rates can be produced by using the same procedure of Example 1 but varying the thickness of Rx 50 tubing. By using an Rx 50 tubing having a wall thickness of 0.5 mm, the implant this produced had a membrane of 0.5 mm.

EXAMPLE 7

The norgestomet implants which do not contain any outer film prepared in Example 2 were dipped in a 1,1,1-trichloroethane solution containing 25% by weight of mixture of an uncured polydimethylsiloxane, platinum catalyst and a methylhydrogensiloxane cross linking agent. The mixture is sold by Dow-Corning as X7-4865 Silastic ®. After drying the implants were air dried and cured at 60° for 3 days. This procedure was repeated until the desired film thickness was obtained. By this procedure, implants were obtained having thickness varying from 0.2 mm to 0.7 mm.

EXAMPLE 8

Norgestomet implants, made in accordance with Example 2 using Q7-4840 Silastic ®, were dipped into a solution containing 25% by weight of X7-4865 Silastic ® and 1,1,1-trichloroethane. Dipping was done several times to obtain an appropriate thickness. The implants were air dried and cured between each dipping, then cut to the desired 1" length and evaluated in-vitro.

Each of the implants containing coatings varying from 0.25 mm to 0.7 mm were evaluated in vitro for their ability to release norgestomet over a period of seven weeks. These implants were also compared to an implant containing no film. Various samples of the implants were checked for their norgestomet elution rate during this seven week period utilizing the following method.

The norgestomet loaded implants were placed in a glass container having a solvent mixture containing 60% by weight distilled deionized water and 40% by weight polyethylene glycol (MW 400) at 37° C. and placed in a controlled temperature environment incubator shaker set at 37° C. and rotating slowly at 50 RPM. The volume of distilled water employed per implant was sufficient to dissolve 4× or more the amount of norgestomet eluted in the time frame of each successive 24 hour test period. The solubility of norgestomet at 25° C. and 37° C. is 97 mcg/ml and 200 mcg/ml respectively. After 24 hours, the implant was removed from the elution vehicle and patted dry on absorbent paper.

The elution vehicle, removed every twenty-four hours was assayed for norgestomet. This assay was carried out by high performance liquid chromatography (HPLC). After removal of the norgestomet elution vehicle, the implant was again placed in a fresh vehicle and maintained in the foregoing manner for twenty hours. The entire procedure was repeated daily for seven weeks. The average daily norgestomet elution rate in mcg per day for each implant having a separate film thickness is given in the following table.

TABLE I

| | ELUTION STUDY OF NORGESTOMET IMPLANTS Q7-4840 COATED WITH X7-4865 SILASTIC | | | | | | |
|---|---|---|---|---|---|---|---|
| | Control Uncoated | 0.25 mm | | 0.5 mm | | 0.7 mm | |
| Weeks | Daily Rate mcg/day | Daily Rate mcg/day | Total Eluted mg | Daily Rate mcg/day | Total Eluted mg | Daily Rate mcg/day | Total Eluted mg |
| 1 | 468 | 217 | 1.52 | 134 | 0.94 | 113 | 0.79 |
| 2 | 290 | 167 | 2.69 | 123 | 1.80 | 100 | 1.49 |
| 3 | 240 | 185 | 3.99 | 105 | 2.54 | 93 | 2.14 |

TABLE I-continued

ELUTION STUDY OF NORGESTOMET IMPLANTS
Q7-4840 COATED WITH X7-4865 SILASTIC

| Weeks | Control Uncoated Daily Rate mcg/day | 0.25 mm Daily Rate mcg/day | 0.25 mm Total Eluted mg | 0.5 mm Daily Rate mcg/day | 0.5 mm Total Eluted mg | 0.7 mm Daily Rate mcg/day | 0.7 mm Total Eluted mg |
| --- | --- | --- | --- | --- | --- | --- | --- |
| 4 | 230 | 165 | 5.15 | 95 | 3.21 | 80 | 2.70 |
| 5 | — | 157 | 6.25 | 105 | 3.95 | 85 | 3.30 |
| 6 | 228 | 157 | 7.35 | 102 | 4.66 | 88 | 3.92 |
| 7 | 215 | 143 | 8.35 | 107 | 5.41 | 88 | 4.54 |
| Slope-Q/T (Average Elution Rate) | | 167 mcg/day | | 107 mcg/day | | 86 mcg/day | |

In FIG. 1, the average daily amount of norgestomet eluted in a given week (mcg/day) was plotted as the ordinate and the thickness of film of the implant was plotted as the abscissa. As seen from FIG. 1 and Table 1, the elution rates in vitro are inversely proportional to the thickness of the coating. As the results indicate X7-4865 coating (0.5 mm or higher) eliminates burst and is a controlling factor in achieving a zero order release rate of norgestomet from a Q7-4840 implant. Also the results demonstrate that to obtain the 150 mcg/day release rate, Q7-4840 implants would have to be coated with 0.3 mm of X7-4865 Silastic ®.

EXAMPLE 9

Implant prepared in Example 7 containing films of 0.25 mm, 0.5 mm and 0.7 mm were compared to the uncoated implant prepared in Example 2 for their ability to release norgestomet over a period of seven weeks. This evaluation was carried in vitro utilizing the weekly average daily elution rate of norgestomet for each implant as determined by the procedure described in Example 8. The results are plotted in FIG. 2. As seen from FIG. 2, there is an initial burst with the uncoated implant whereas this burst is substantially reduced by a 0.25 mm film. On the other hand films having thickness of 0.5 mm and 0.7 mm provide a uniform rate of norgestomet release without any substantial initial burst.

EXAMPLE 10

The one inch implant prepared in Example 2 without any film as well as the one inch implant with a 8 mil sheath (film thickness 0.2 mm) prepared in Example 1 and the one inch implant with a 20 mil sheath (film thickness 0.5 mm) prepared in Example 6 were inserted into cattle and their norgestomet elution rate in cattle was compared. The procedure for implanting and then removing these implants in cattle was as follows.

Steps in Implanting

1. Restrain animal in cattle chute.
2. Disinfect implanter in tray with alcohol or disinfectant.
3. Prepare implant site on caudal (outer) surface of the ear midway between tip of ear and base in an area avoiding vessels. Clip hair, if hair is long.
4. Disinfect skin with alcohol.
5. Remove implanter from disinfectant; shake off excess solution.
6. Remove implant from container and place in implanter. Handle implant as little as possible to decrease chance of contamination.
7. Support ear with one hand and with beveled side of needle away from skin, pick-up skin with the point of the needle and penetrate skin. It is important not to penetrate or puncture the cartilage of the ear.
8. With the needle parallel to the ear surface, push the needle between skin and cartilage for the entire length of the needle.
9. While pushing the plunger of the implanter, eject the implant under the skin while simultaneously withdrawing the needle from beneath the skin.
10. Check to make sure implant is in proper position, under skin about ¼-½" from needle hole.

Steps in Removing Implant

1. Restrain the animal as noted above.
2. Disinfect skin over implant area.
3. Use sharp-pointed scissors to make a small incision in the skin at the end of the implant.
4. Using your thumb, push the implant out the hole until the implant can be seen. Using forceps, remove the impact carefully.

After removal of the implantation from each of the animals at various periods of time, the elution rate of norgestomet when implanted in the animal was determined by the following procedure.

Chromatographic Conditions

| Column: | 5 Micro-meters silica, 4.6 mm ID × 250 mm. |
| --- | --- |
| HPLC mobile phase: | 10% ethanol in heptane |
| Detection: | UV @ 240 nm |
| Flow rate: | 1.5 ml/minute |
| Injection volume: | 20 ul |
| Approximate retention time: | 4 minutes |

Standard Preparation

Weigh 10.0 mg of norgestomet reference material into a 50 ml volumetric flask. Dissolve and dilute to volume with 1:1 hexane: ethanol (Standard Solution 1). Pipet 3.0 ml of standard solution 1 into a 50 ml volumetric flask and dilute to volume with HPLC mobile phase (Standard Solution 2).

Sample Preparation

Weigh the implant. Take approximately ⅓ of the total implant and cut into very thin (less than 1 mm) pieces. Weigh and transfer the pieces into a 50 ml volumetric flask. Add 25 ml of 1:1 ethanol: hexane and shake overnight at 37° C. Cool to room temperature and dilute to volume with 1:1 ethanol:hexane (Sample Solution 1). Pipet 3.0 ml of Sample Solution 1 into a 50 ml volumetric flask and dilute to volume with HPLC mobile phase (Sample Solution 2).

Procedure

Chromatograph Standard Solution 2 and Sample Solution 2 using the above conditions. The amount of norgestomet in the implant is calculated with an external standard calculation using Sample Solution 2 and Standard Solution 2 peak heights.

From this assay the cumulative mean release rate (mcg/day) for each implant was determined at 4, 8, 12, 14, 16 and 20 weeks. The results are plotted in FIG. 3. As seen from FIG. 3 the one inch implant caused an initial burst of norgestomet whereas with the implants with 0.2 mm and 0.3 mm films produced a zero order rate of norgestomet release with no initial burst.

I claim:

1. A device for delivering a drug selected from the group consisting of steroids, alkaloids, fatty acids, vitamins, antibodies and birth control agents over a prolonged period of time, said device being adapted to be implanted subcutaneously and comprising an inner rod shaped solid polymer matrix having an elongated body and two ends, said matrix having solid particles of said drug dispersed throughout the matrix, an outer polymer membrane as a coating or laminate chemically bonded to the surface of the elongated body of the matrix. each of said matrix and membrane being a copolymer of methyl vinyl siloxane and dimethylpolysiloxane cross-linked by the same cross-linking agent and with all of said drug being present within the matrix.

2. The device of claim 1 wherein said polymer membrane forms an outer coating on said solid matrix.

3. The device of claim 2 wherein the polymer materials which form the matrix and membrane are cross-linked with a polyalkyl hydrogensiloxane cross-linking agent catalyst.

4. The device of claim 3 wherein said drug is norgestomet.

5. The device of claim 1 wherein said polymer membrane is an outer film chemically bonded to the inner matrix.

6. The device of claim 5 wherein the polymer material which form the matrix and membrane are cross-linked with a polymethylhydrogensiloxane cross-linking agent and a platinum catalyst.

7. The device of claim 6 wherein said drug is norgestomet.

* * * * *